United States Patent
Chilkoti

(10) Patent No.: US 8,367,314 B2
(45) Date of Patent: *Feb. 5, 2013

(54) NON-FOULING POLYMERIC SURFACE MODIFICATION AND SIGNAL AMPLIFICATION METHOD FOR BIOMOLECULAR DETECTION

(75) Inventor: Ashutosh Chilkoti, Durham, NC (US)

(73) Assignee: Duke University, Durham, NC (US)

( * ) Notice: Subject to any disclaimer, the term of this patent is extended or adjusted under 35 U.S.C. 154(b) by 430 days.

This patent is subject to a terminal disclaimer.

(21) Appl. No.: 12/644,197

(22) Filed: Dec. 22, 2009

(65) Prior Publication Data

US 2010/0099579 A1 Apr. 22, 2010

Related U.S. Application Data

(62) Division of application No. 11/521,651, filed on Sep. 15, 2006, now Pat. No. 7,713,689.

(60) Provisional application No. 60/717,430, filed on Sep. 15, 2005.

(51) Int. Cl.
*C12Q 1/00* (2006.01)

(52) U.S. Cl. .......................................................... 435/4

(58) Field of Classification Search ........................ None
See application file for complete search history.

(56) References Cited

U.S. PATENT DOCUMENTS

| | | | |
|---|---|---|---|
| 4,940,737 A * | 7/1990 | Braatz et al. .................. 521/103 |
| 5,582,981 A | 12/1996 | Toole et al. |
| 5,840,867 A | 11/1998 | Toole et al. |
| 6,413,587 B1 | 7/2002 | Hawker et al. |
| 6,423,465 B1 | 7/2002 | Hawker et al. |
| 6,444,254 B1 | 9/2002 | Chilkoti et al. |
| 6,512,060 B1 | 1/2003 | Matyjaszewski et al. |
| 6,541,580 B1 | 4/2003 | Matyjaszewski et al. |
| 6,582,926 B1 | 6/2003 | Chilkoti |
| 6,649,138 B2 | 11/2003 | Adams et al. |
| 6,815,078 B2 | 11/2004 | Qiao et al. |
| 6,867,289 B1 | 3/2005 | Luxon et al. |
| 6,884,628 B2 * | 4/2005 | Hubbell et al. ................ 436/518 |
| 7,713,689 B2 * | 5/2010 | Chilkoti ............................ 435/4 |
| 2002/0031776 A1 | 3/2002 | Tullis et al. |
| 2003/0059537 A1 | 3/2003 | Chilkoti |
| 2003/0108879 A1 | 6/2003 | Klaerner et al. |
| 2003/0143535 A1 | 7/2003 | Lyamichev et al. |
| 2003/0185741 A1 | 10/2003 | Matyjaszewski et al. |
| 2004/0197899 A1 | 10/2004 | Gomez et al. |
| 2004/0242023 A1 | 12/2004 | Yan et al. |
| 2005/0100987 A1 | 5/2005 | Evans et al. |
| 2005/0164205 A1 | 7/2005 | Puskas |
| 2005/0282242 A1 | 12/2005 | Rothstein et al. |
| 2006/0057180 A1 | 3/2006 | Chilkoti et al. |

OTHER PUBLICATIONS

International Search Report and Written Opinion, PCT/US06/36102, Aug. 6, 2007.
Nath N. et al. Surface engineering strategies for control of protein and cell interactions. Surface Science (2004), vol. 570, pp. 98-110.
Ma H et al. "Non-Fouling" Oligo(ethylene glycol)—Functionalized Polymer Brushes Synthesized by Surface-Initiated Atom Transfer Radical Polymerization. Advanced Materials (Feb. 17, 2004), vol. 16, No. 4, pp. 338-341.
Kane R S et al. Kosmotropes Form the Basis of Protein-Resistant Surfaces. Langmuir (2003), vol. 19, pp. 2388-2391.

* cited by examiner

*Primary Examiner* — Ann Lam
(74) *Attorney, Agent, or Firm* — Myers Bigel Sibley & Sajovec, PA

(57) ABSTRACT

An article such as a biosensor having a nonfouling surface thereon is described. The article comprises: (a) a substrate having a surface portion; (b) a linking layer on the surface portion; (c) a polymer layer comprising brush molecules formed on the linking layer; and (d) optionally but preferably, a first member of a specific binding pair (e.g., a protein, peptide, antibody, nucleic acid, etc.) coupled to the brush molecules. The polymer layer is preferably formed by the process of surface-initiated polymerization (SIP) of monomeric units thereon. Preferably, each of the monomeric units comprises a monomer (for example, a vinyl monomer) core group having at least one protein-resistant head group coupled thereto, to thereby form the brush molecule on the surface portion. Methods of using the articles are also described.

17 Claims, 6 Drawing Sheets

A)

Poly(OEGMA) (POEGMA)

Poly(vinylbenzyl chloride) (PVBC)

B)

NON-FOULING POLYMERIC SURFACE MODIFICATION AND SIGNAL AMPLIFICATION METHOD FOR BIOMOLECULAR DETECTION

RELATED APPLICATIONS

This application claims priority to and is a divisional of U.S. patent application Ser. No. 11/521,651, filed Sep. 15, 2006 now U.S. Pat. No. 7,713,689, now allowed, and also claims the benefit of U.S. Provisional Patent Application Ser. No. 60/717,430; filed Sep. 15, 2005, the disclosure of each of which is incorporated by reference herein in its entirety.

This application is related to Ashutosh Chilkoti and Hongwei Ma, A tunable nonfouling surface of oligoethylene glycol, U.S. patent application Ser. No. 10/783,054, filed Feb. 20, 2004, the disclosure of which is incorporated by reference herein in its entirety.

This invention was made with Government support under grant no. R01 CI-00097 from the Centers for Disease Control/NCID. The United States Government has certain rights to this invention.

FIELD OF THE INVENTION

This invention relates to a non-fouling polymeric surface modification and signal amplification method for ultra-sensitive biomolecular detection.

BACKGROUND OF THE INVENTION

Glass and silicon oxide are widely used substrates for biosensors, clinical immunoassay diagnostics, and cell culture (Ratner, Schoen et al. 1996) and as solid supports for the synthesis of peptides, carbohydrates, and DNA (Seeberger and Haase 2000). The modification of silicon oxide to modulate protein and cell interactions has proven to challenging for a number of technical reasons: 1) the formation of silane self-assembled monolayers (SAMs), the most common route to functionalize glass and other metal oxides, is complicated by the sensitivity of most silanes to humidity and their propensity to form polymeric multi-layers (Wasserman, Tao et al. 1989; Ulman 1996). 2) As is typical to most "grafting to" approaches, the passivation of silicon oxide by grafting polyethylene glycol (PEG) to the surface using silane chemistry (Emoto, Harris et al. 1996; Yang, Galloway et al. 1999) does not provide a high surface density of PEG due to the excluded volume effect (Knoll and Hermans 1983). Consequently, grafted PEG coatings on glass decrease the adsorption of proteins, but do not reduce their adsorption below the nominal limit of several $ng/cm^2$ (Zhu, Jun et al. 2001). Several approaches such as the sequential grafting of PEGs of different chain lengths (Nagasaki, Ishii et al. 2001) and cloud-point grafting of PEG (Kingshott, Thissen et al. 2002) have been taken to solve this problem, but only with limited success. 3) It is also difficult to stamp silanes onto glass with the ease and reproducibility with which alkanethiols can be patterned by micro-contact printing and other soft lithography methods so that the patterning of PEG on to glass by soft lithography has only been marginally successful (Xia, Mrksich et al. 1995; StJohn and Craighead 1996).

For the detection of a variety of biological molecules such as protein, RNA, and DNA in complex biological fluids, the minimization of non-specific protein binding plays a very important in improving the detection limit and sensitivity. The reduction of adsorption of protein and other biomolecules is important for the development of interfacial sensors for two reasons: first, for the broad class of sensors that are label-free, i.e., in which the binding event is directly transduced as the detected signal (e.g., surface plasmon resonance (SPR) spectroscopy, localized or nanoparticle-based surface plasmon resonance (nanoSPR), surface enhanced Raman scattering (SERS), ellipsometry, gravimetric sensors such as quartz-crystal microbalance dissipation (QCM-D) and surface acoustic wave (SAW) sensors, etc.) reduction of protein adsorption to ultra-low levels (<1 ng/sq. cm) is critical to generate a high signal-to-noise ratio (SNR) by reducing the noise due to adventitious adsorption. For the class of interfacial sensors that use a label to generate the detected signal, the elimination of background adsorption is similarly important to reduce noise. Finally, for the class of sensors that incorporate an amplification step prior to or during generation of the detected signal, the effective elimination of adventitious adsorption or binding of biomolecules or other reagents is critical, as adventitiously bound molecules can be amplified, so that the increase in signal (S) afforded by the amplification step is in many cases compromised by the concomitant amplification of the background noise (N), so that the gains in SNR are modest, at best.

The increasing technological push towards ultra-sensitive detection in biomolecular arrays—DNA, protein and carbohydrate—similarly requires extremely low background signals so that a high SNR can be attained (Zhu and Snyder 2003). However, most commercially available chemical surface modifications usually have high auto-fluorescence or non-specific binding of reagents and analytes. This issue is increasingly crucial when the spot size of commonly used microarrays becomes smaller and smaller, even down to the sub-micron length scale. Although some of the current surface modification techniques work well for microarrays (Zhu and Snyder 2003), the routine use of micro- and nano-arrays for biomolecules still poses substantial challenges in engineering a detection system that is capable of resisting non-specific adsorption of biomolecules down to the $pg/cm^2$ level and allows direct detection of analytes without elaborate and expensive amplification techniques.

SUMMARY OF THE INVENTION

A first aspect of the present invention is an article (preferably a biomolecular detector or biosensor such as a microarray) having a nonfouling surface thereon, the article comprising:

(a) a substrate having a surface portion;

(b) a linking layer on the surface portion; and (c) a polymer layer formed on the linking layer, preferably by the process of surface-initiated polymerization (SIP) of monomeric units thereon. Preferably, each of the monomeric units comprises a monomer (for example, a vinyl monomer) core group having at least one protein-resistant head group coupled thereto, to thereby form a brush molecule on the surface portion. The brush molecule preferably comprises a stem formed from the polymerization of the monomer core groups, and a plurality of branches foamed from the head group projecting from the stem; and (d) optionally but preferably, a first member of a specific binding pair (e.g., a protein, peptide, antibody, nucleic acid, etc.) coupled to the brush molecule.

In some embodiments, the member of a specific binding pair further comprises an extended nucleic acid conjugated thereto, the extended nucleic acid produced by the process of enzymatic extension with terminal transferase (TdTase).

In some embodiments, wherein the first member is a first nucleic acid, the detector optionally further comprising a second nucleic acid as a second member of the binding pair hybridized to the first member. Some embodiments thereof further comprise an extended nucleic acid produced by the process of enzymatic extension with terminal transferase coupled to either the first or second nucleic acid.

In some embodiments, particularly where the first member of the binding pair is a protein or peptide, the detector further comprises: a second member of the specific binding pair coupled to the first member of the specific binding pair; an antibody specifically bound to the second member to form a sandwich, the antibody having a first nucleic acid conjugated thereto; and an extended nucleotide coupled to the first nucleotide, the extended nucleic acid produced by the process of enzymatic extension with terminal transferase.

A second aspect of the present invention is a method of making an article (preferably a biomolecular detector such as a microarray) having a nonfouling surface thereon, the method comprising: (a) providing a substrate having a surface portion; (b) depositing a linking layer on the surface portion; and (c) forming a polymer layer on the linking layer by the process of surface-initiated polymerization of monomeric units thereon, with each of the monomeric units comprising a monomer (for example, a vinyl monomer) core group having at least one protein-resistant head group coupled thereto, to thereby form a brush molecule on the surface portion; the brush molecule comprising a stem formed from the polymerization of the monomer core groups, and a plurality of branches formed from the hydrophilic head group projecting from the stem.

In some embodiments the polymer comprises a copolymer of methoxy-terminated OEGMA and hydroxy-terminated OEGMA. Such embodiments may further comprise the step of coupling a compound (e.g., a first member of a specific binding pair) having an amine group to the hydroxy group via the amine group. In other embodiments the polymer comprises of vinyl monomer bearing other head groups such as hydroxyl (OH), glycerol, or groups known in the art as kosmotropes (see, e.g., Kane et al., infra).

In some embodiments the copolymer is synthesized on the surface portion by SI-ATRP, wherein the hydroxy groups are converted to COOH groups by any suitable reaction such as reaction with N-hydroxy succinimide (NHS), and wherein the amine groups are coupled to the COOH.

In some embodiments the polymer comprises a copolymer of OEGMA and sodium methacrylate, the copolymer having sodium carboxylate groups. In some embodiments the sodium carboxylate group is converted to a COOH group by reaction with an acid such as HCl, and a protein or peptide is coupled to the COOH groups via their N-terminal amine or lysine residues (by any suitable reaction such as NHS/EDC coupling).

In some embodiments the polymer is OEGMA, the OEGMA containing of thioester groups; and wherein the member of a specific binding pair is coupled to the thioester group. In some embodiments the first member of a specific binding pair is a protein or peptide having an N-terminal cysteine, and wherein the coupling step is carried out by reaction with the N-terminal cysteine with the thioester by any suitable reaction, such as intein protein ligation (IPL) or native chemical ligation.

In some embodiments wherein the polymer is OEGMA, the OEGMA contains cysteine groups, and the member of a specific binding pair contains a C-terminal thioester, the coupling step is carried out by reaction of the C-terminal cysteine with the thioester by any suitable reaction, such as intein protein ligation (IPL) or native chemical ligation.

In some embodiments of the invention, the surface portion comprises a material selected from the group consisting of metals, metal oxides, semiconductors, polymers, silicon, silicon oxide, and composites thereof.

In some embodiments of the invention the linking layer is continuous; in some embodiments of the invention the linking layer is patterned. In some embodiments of the invention the linking layer is a self-assembled monolayer (SAM). In some embodiments of the invention the linking layer comprises an initiator-terminated alkanethiol.

In some embodiments of the invention the surface-initiated polymerization is carried out by atom transfer radical polymerization (ATRP); in some embodiments of the invention the surface-initiated polymerization is carried out by free radical polymerization.

In some embodiments, the article further comprises a protein, peptide, oligonucleotide or peptide nucleic acid covalently coupled to the brush molecule. In some embodiments the protein, peptide, oligonucleotide or peptide nucleic acid coupled to the brush molecule or to the surface consist of or consist essentially of a single preselected molecule (this is, one such molecule is coupled to the surface portion via the brush molecule, to the exclusion of other different molecules). The preselected molecule may be a member of a specific binding pair, such as a receptor.

A further aspect of the invention is a method of detecting a second member of a specific binding pair nucleotide in a sample, comprising the steps of: (a) providing a detector as described herein; (b) contacting a sample (e.g., an aqueous sample or biological fluid) suspected of containing the second member to the detector; and then (c) determining the presence or absence of binding of the second member to the first member, the presence of binding indicating the presence of the second member in the sample. The determining step can be carried out by any suitable technique, but preferably involves directly or indirectly conjugating an elongated nucleic acid to the second member, the elongated nucleic acid produced by the process of enzymatic extension with terminal transferase.

In some embodiments the first member is a probe nucleotide and second member is a target nucleotide. In such embodiments the determining step may comprise (i) elongating the target nucleotide with terminal transferase to produce an elongated nucleic acid, and then (ii) detecting the presence or absence of the elongated nucleic acid.

In some embodiments the probe nucleotide comprises a beacon portion and a second portion, with the beacon portion folded by hybridization to the second portion, wherein the binding of the target nucleotide to the probe nucleotide unfolds the beacon portion to produce a free end terminal for extension with terminal transferase. In such embodiments the deter mining step may comprise: (i) elongating the beacon portion with terminal transferase to produce an elongated nucleic acid, and then (ii) detecting the presence or absence of the elongated nucleic acid.

In some embodiments the second member is a protein or peptide. In such embodiments the determining step may comprise: (i) specifically binding an antibody to the first member to form a sandwich, the antibody having a first nucleic acid conjugated thereto, (ii) elongating the first nucleici acid with terminal transferase to produce an elongated nucleic acid, and then (iii) detecting the presence or absence of the elongated nucleic acid.

An advantage of the foregoing methods is the variety of techniques by which the detecting step can be carried out. For example, the detecting step may be carried out by: (a) ellipsometry; (b) surface plasmon resonance (SPR); (c) localized surface plasmon resonance using noble metal nanoparticles in solution or on a transparent surface; (d) surface acoustic wave (SAW) devices; (e) quartz-crystal microbalance with dissipation (QCM-D) (e) atomic force microscopy, (f) detection of radiolabeled nucleotides incorporated in the elongated portion for radioactive detection, (g) detection of stable isotope labeled nucleotides in the elongated nucleic acid by mass spectrometry, (h) incorporation of fluorophores into the elongated nucleic acid and fluorescent detection, (i) incorporation of nucleotides containing amino acids to which fluorophores are attached into the elongated nucleic acid and fluorescent detection, or (j) indirectly by hybridization of the elongated nucleic acid with a labeled complementary nucleic acid, and subsequent detection of the complementary nucleic acid, wherein the complementary nucleic acid is labeled by coupling to a metal nanoparticle, quantum dot, fluorophore, or radionuclide, etc.

Still other aspects of the present invention are explained in greater detail below.

DETAILED DESCRIPTION OF THE PREFERRED EMBODIMENTS

Figure 1:
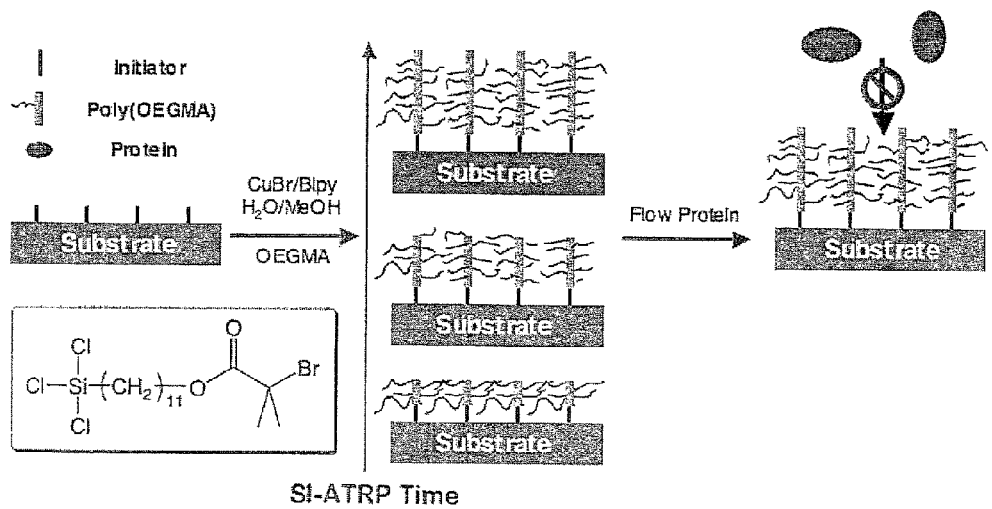
FIG. 1. Schematic illustration of "SI-ATRP of OEGMA" strategy for creating functionalized non-fouling surfaces and molecular structure of silane initiator (11-(2-Bromo-2-methyl)propionyloxy)undecyl trichlorosilane.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs.

The disclosures of all United States patents cited herein are incorporated by reference in their entirety.

1. Definitions

"SI-ATRP" as used herein means surface initiated atom transfer radical polymerization.

"OEGMA" as used herein refers to oligo(ethylene glycol) methyl methacrylate.

"Biological fluid" as used herein may be any fluid of human or animal origin, including but not limited to blood, blood plasma, peritoneal fluid, cerebrospinal fluid, tear, mucus, and lymph fluid. Biological fluids generally contain a mixture of different proteins therein, and typically contain other constituents such as other cells and molecules. Biological fluids may be in their natural state or in a modified state by the addition of ingredients such as reagents or removal of one or more natural constituents (e.g., blood plasma).

"Kosmotrope", while originally used to denote a solute that stabilized a protein or membrane, is also used by those skilled in the art, and is used herein, to denote a substituent or "head group" which, when deposited on a surface, renders that surface protein-resistant. See, e.g., R. Kane. P. Deschatelets and G. Whitesides, *Kosmotropes Form the Basis of Protein-Resistant Surfaces, Langmuir* 19, 2388-2391 (2003). Numerous kosmotropes are known and examples include but are not limited to OEGMA.

"Polymer" as used herein is intended to encompass any type of polymer, including homopolymers, heteropolymers, co-polymers, ter-polymers, etc., and blends, combinations and mixtures thereof.

"Specific binding pair" as used herein refers to two compounds that specifically bind to one another, such as (functionally): a receptor and a ligand (such as a drug), an antibody and an antigen, etc.; or (structurally): protein or peptide and protein or peptide; protein or peptide and nucleic acid; and nucleotide and nucleotide etc.

2. Substrates

The present invention can be utilized to forms surfaces on a variety of different types of substrates.

In some embodiments, the article is a label-free optical or mass detector (e.g., a surface plasmon resonance energy detector, an optical wave guide, an ellipsometry detector, etc.) and the surface is a sensing surface (e.g., a surface portion that would be in contact with a biological fluid). Examples of such articles include but are not limited to those described in U.S.

Pat. Nos. 6,579,721; 6,573,107; 6,570,657; 6,423,055; 5,991,048; 5,822,073; 5,815,278; 5,625,455; 5,485,277; 5,415,842; 4,844,613; and 4,822,135.

In other embodiments, the article is a biosensor, an assay plate, or the like. For example, the present invention may be utilized with optical biosensors such as described in U.S. Pat. Nos. 5,313,264 to Ulf et al., 5,846,842 to Herron et al., 5,496,701 to Pollard-Knight et al., etc. The present invention may be utilized with potentiometric or electrochemical biosensors, such as described in U.S. Pat. No. 5,413,690 to Kost, or PCT Application WO98/35232 to Fowlkes and Thorp. The present invention may be utilized with a diamond film biosensor, such as described in U.S. Pat. No. 5,777,372 Thus, the solid support may be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. For example, the solid support may be comprised of polyethylene, polytetrafluoroethylene, polystyrene, polyethylene terephthalate, polycarbonate, gold, silicon, silicon oxide, silicon oxynitride, indium, tantalum oxide, niobium oxide, titanium, titanium oxide, platinum, iridium, indium tin oxide, diamond or diamond-like film, etc.

The present invention may be utilized with substrates for "chip-based" and "pin-based" combinatorial chemistry techniques. All can be prepared in accordance with known techniques. See. e.g., U.S. Pat. No. 5,445,934 to Fodor et al., U.S. Pat. No. 5,288,514 to Ellman, and U.S. Pat. No. 5,624,711 to Sundberg et al., the disclosures of which are incorporated by reference herein in their entirety.

Substrates as described above can be formed of any suitable material, including but not limited to a material selected from the group consisting of metals, metal oxides, semiconductors, polymers (particularly organic polymers in any suitable form including woven, nonwoven, molded, extruded, cast, etc.), silicon, silicon oxide, and composites thereof.

Polymers used to form substrates as described herein may be any suitable polymer, including but not limited to: poly(ethylene) (PE), poly(propylene) (PP), cis and trans isomers of poly(butadiene) (PB), cis and trans isomers of poly(isoprene), poly(ethylene terephthalate) (PET), polystyrene (PS), polycarbonate (PC), poly(epsilon-caprolactone) (PECL or PCL), poly(methyl methacrylate) (PMMA) and its homologs, poly(methyl acrylate) and its homologs, poly(lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, and combinations and copolymers thereof, etc.

If desired or necessary, the substrate may have an additional layer such as a gold or an oxide layer formed on the relevant surface portion to facilitate the deposition of the linking layer, as discussed further below.

3. Linking (or "Anchor") Layers

Anchor layers used to carry out the present invention are generally fouled from a compound comprising an anchor group coupled (e.g., covalently coupled) to an initiator (e.g., directly coupled or coupled through an intermediate linking group). The choice of anchor group will depend upon the surface portion on which the linking layer is formed, and the choice of initiator will depend upon the particular reaction used to form the brush polymer as discussed in greater detail below.

The anchoring group may be selected to covalently or non-covalently couple the compound or linking layer to the surface portion. Non-covalent coupling may be by any suitable secondary interaction, including but not limited to hydrophobic bonding, hydrogen bonding, Van der Waals interactions, ionic bonding, etc.

Examples of substrate materials and corresponding anchoring groups include, for example, gold, silver, copper, cadmium, zinc, palladium, platinum, mercury, lead, iron, chromium, manganese, tungsten, and any alloys thereof with sulfur-containing functional groups such as thiols, sulfides, disulfides (e.g., —SR or —SSR where R is H of alkyl, typically lower alkyl, or aryl), and the like; doped or undoped silicon with silanes and chlorosilanes (e.g., —SiR$_2$Cl wherein R is H or alkyl, typically lower alkyl, or aryl); metal oxides such as silica, alumina, quartz, glass, and the like with carboxylic acids as anchoring groups; platinum and palladium with nitrites and isonitriles; and copper with hydroxamic acids. Additional suitable functional groups suitable as the anchoring group include benzophenones, acid chlorides, anhydrides, epoxides, sulfonyl groups, phosphoryl groups, hydroxyl groups, phosphonates, phosphonic acids, amino acid groups, amides, and the like. See, e.g., U.S. Pat. No. 6,413,587.

Any suitable initiator may be incorporated into the anchoring group by introduction of a covalent bond at a location non-critical for the activity of the initiator. Examples of such initiators include, but are not limited to, bromoisobutyrate, polymethyl methacrylate-Cl, polystyrene-Cl, AIBN, 2-bromoisobutyrate, chlorobenzene, hexabromomethyl benzene, hexachloromethyl benzene, dibromoxylene, methyl bromoproprionate. Additional examples of initiators include those initiators described in U.S. Pat. No. 6,413,587 to Hawker (particularly at columns 10-11 thereof) and those initiators described in U.S. Pat. No. 6,541,580 to Matyjaszewski et al.

As noted above, a linking group or "spacer" may be inserted between the anchoring group and initiator. The linker may be polar, nonpolar, positively charged, negatively charged or uncharged, and may be, for example, saturated or unsaturated, linear or branched alkylene, aralkylene, alkarylene, or other hydrocarbylene, such as halogenated hydrocarbylene, particularly fluorinated hydrocarbylene. Preferred linkers are simply saturated alkylene of 3 to 20 carbon atoms, i.e., —(CH$_2$)$_4$— where n is an integer of 3 to 20 inclusive. See, e.g., U.S. Pat. No. 6,413,587. Another preferred embodiment of the linker is an oligoethyleneglycol of 3 to 20 units, i.e., (CH$_2$CH$_2$O)$_n$ where n ranges from 3 to 20.

The anchoring layer may be deposited by any suitable technique. It may be deposited as a self-assembled monolayer. It may be created by modification of the substrate by chemical reaction (see, e.g., U.S. Pat. No. 6,444,254 to Chilkoti et al.) or by reactive plasma etching or corona discharge treatment. It may be deposited by a plasma deposition process. It may be deposited by spin coating or dip coating. It may be deposited by spray painting. It may also be deposited by deposition, printing, stamping, etc. It may be deposited as a continuous layer or as a discontinuous (e.g., patterned) layer.

In some preferred embodiments, the substrate is glass, silicon oxide or other inorganic or semiconductor material (e.g., silicon oxide, silicon nitride) and compound semiconductors (e.g., gallium arsenide, and indium gallium arsenide) used for microarray production.

In some preferred embodiment, the anchoring group is a silane or chlorosilane (e.g., —SiR$_2$Cl wherein R is H or alkyl, typically lower alkyl, or aryl).

4. Brush Polymer Formation

The brush polymers are, in general, formed by the polymerization of monomeric core groups having a protein-resistant head group coupled thereto.

Any suitable core vinyl monomer polymerizable by the processes discussed below can be used, including but not limited to styrenes, acrylonitriles, acetates, acrylates, methacrylates, acrylamides, methacrylamides, vinyl alcohols, vinyl acids, and combinations thereof.

Protein resistant groups may be hydrophilic head groups or kosmotropes. Examples include but are not limited to oligosaccharides, tri(propyl sulfoxide), hydroxyl, glycerol, phosphorylcholine, tri(sarcosine) (Sarc), N-acetylpiperazine, permethylated sorbitol, hexamethylphosphoramide, an intramolecular zwitterion (for example, —CH$_2$N$^+$(CH$_3$)$_2$CH$_2$CH$_2$CH$_2$SO$_3^-$) (ZW), and mannitol.

Additional examples of kosmotrope protein resistant head groups include, but are not limited to:
- -(EG)$_6$OH;
- —O(Mannitol);
- —C(O)N(CH$_3$)CH$_2$(CH(OCH$_3$))$_4$CH$_2$OCH$_3$;
- —N(CH$_3$)$_3^+$Cl$^-$/—SO$_3^-$Na$^+$;
- —N(CH$_3$)$_2^+$CH$_2$CH$_2$SO$_3^-$;
- —C(O)Pip(NAc);
- —N(CH$_3$)$_2^+$CH$_2$CO$_2^-$;
- —O([Blc-α(1,4)-Glc-β(1)-]);
- —C(O)(N(CH$_3$)CH$_2$C(O))$_3$N(CH$_3$)$_2$;
- —N(CH$_3$)$_2^+$CH$_2$CH$_2$CH$_2$SO$_3^-$;
- —C(O)N(CH$_3$)CH$_2$CH$_2$N(CH$_3$)P(O)(N(CH$_3$)$_2$)$_2$; and
- —(S(O)CH$_2$CH$_2$CH$_2$)$_3$S(O)CH$_3$.

See, e.g., R. Kane et al., *Langmuir* 19, 2388-91 (2003)(Table 1).

A particularly preferred protein resistant head group is poly(ethylene glycol), or "PEG", for example PEG consisting of from 3 to 20 monomeric units.

Free radical polymerization of monomers to form brush polymers can be carried out in accordance with known techniques, such as described in U.S. Pat. No. 6,423,465 to Hawker et al.; U.S. Pat. No. 6,413,587 to Hawker et al.; U.S. Pat. No. 6,649,138 to Adams et al.; US Patent Application 2003/0108879 to Klaerner et al.; or variations thereof which will be apparent to skilled persons based on the disclosure provided herein.

Atom or transfer radical polymerization of monomers to fowl brush polymers can be carried out in accordance with known techniques, such as described in U.S. Pat. No. 6,541,580 to Matyjaszewski et al.; U.S. Pat. No. 6,512,060 to Matyjaszewski et al.; or US Patent Application 2003/0185741 to Matyjaszewski et al., or variations thereof which will be apparent to skilled persons based on the disclosure provided herein.

In general, the brush molecules formed by the processes described herein will be from 2 or 5 up to 50 or 100 nanometers in length, or more, and will be deposited on the surface portion at a density of from 10, 20 or 40 up to 100, 200 or 500 milligrams per meter$^2$, or more.

In some preferred embodiments, the polymer layer is formed by SI-ATRP of OEGMA to form a poly(OEGMA) film. In particularly preferred embodiments, the polymer layer is a functionalized poly(OEGMA) film prepared (preferably in a single step) by copolymerization of a methacrylate and methyl terminated OEGMA. For the copolymer, poly (sodium methacrylate-co-OEGMA), or the like, the carboxylate can be converted to carboxyl acid by incubation of the copolymer in an acid such as HCl, resulting in poly(MAA-co-OEGMA)(MAA: methacrylate acid). The poly(MAA-co-OEGMA) can be further converted to the ester in accordance with known techniques.

In other particularly preferred embodiment, copolymers of methoxy-terminated OEGMA with OH-terminated OEGMA, and the OH is directly used to conjugate molecules of all types via their available amine groups using well known coupling reactions, such as tresyl chloride conjugation and CDI chemistry. In other particularly preferred embodiments, copolymers of methoxy-OEGMA and OH-terminated OEGMA are synthesized on the substrate by SI-ATRP, and the OH groups are converted to COOH groups by reaction with N-hydroxy succinimide (NHS), and the COOH groups are used as sites for attachment of molecules via available amine groups on the molecule.

In other preferred embodiments, the OEGMA is synthesized to directly contain a fraction of thioester groups, so as to permit direct attachment of any molecule but preferentially a protein or peptide via reaction with their N-terminal cysteine using intein protein ligation (IPL) or native chemical ligation. Similarly, this approach can be reversed, so that the OEGMA polymer could contain, either as a consequence of incorporation during SI-ATRP using a suitable OEGMA-functionalized monomer or by conversion of incorporated groups (e.g., but not limited to OH or COOH groups) to a cysteine, so that a molecules such as a protein or peptide contains a C-terminal thioester, as is typically obtained by intein-mediated cleavage of a target protein or peptide of an intein fusion could be covalently attached via its thioester to the cysteine groups presented on the termini of the OEGMA polymer.

Proteins, peptides, antibodies, oligonucleotides or nucleic acids (such as DNAs) (e.g., 3-50 nucleotides in length) or other members of a binding pair can be deposited on the polymer layer, typically after introduction of a carboxyl group therein, by any suitable technique such as microprinting or microstamping. Microarrays or nanoarrays of oligonucleotides can be formed on the substrates by any suitable technique, such as e-beam lithography.

5. Uses and Applications of Articles

In some embodiments the present invention is utilized by (a) providing an article as described herein, the article further comprising a first member of a specific binding pair such as a protein, peptide, oligonucleotide, peptide nucleic acid or the like covalently coupled to the brush molecule, the first member preferably consisting essentially of a single preselected molecule; and then (b) contacting the article to a biological fluid or other composition containing a second member of the specific binding pair, wherein the second member of the specific binding pair binds to the surface portions. Such uses are particularly appropriate where the article is a sensor or biosensor as described in greater detail above.

Binding of the second member of the specific binding pair can be achieved by any suitable technique. In some embodiments the binding is preferably carried out by sandwich assay. In some embodiments the binding may be detected by extension of a nucleic acid such as a DNA with terminal transferase to form an extended nucleic acid, which extended nucleic acid may be detected by any suitable technique. Terminal transferase (e.g., TdTase) is known, and methods of elongating nucleic acids (or shorter oligonucleotides), to produce extended nucleic acids (or longer oligonucleotides) or extension products, and methods of detecting such extension products can be carried out in accordance with known techniques or variations thereof that will be apparent to those skilled in the art in view of the instant disclosure and known methods of using terminal transferase as described in (for example) U.S. Pat. Nos. 6,911,305; 6,864,060; 6,709,816; 6,642,375; 6,406,890; 6,323,337; 6,136,531; 5,824,514; 5,397,698; and 5,344,757.

The present invention is explained in greater detail in the following non-limiting Examples.

EXPERIMENTAL

Figure 2:
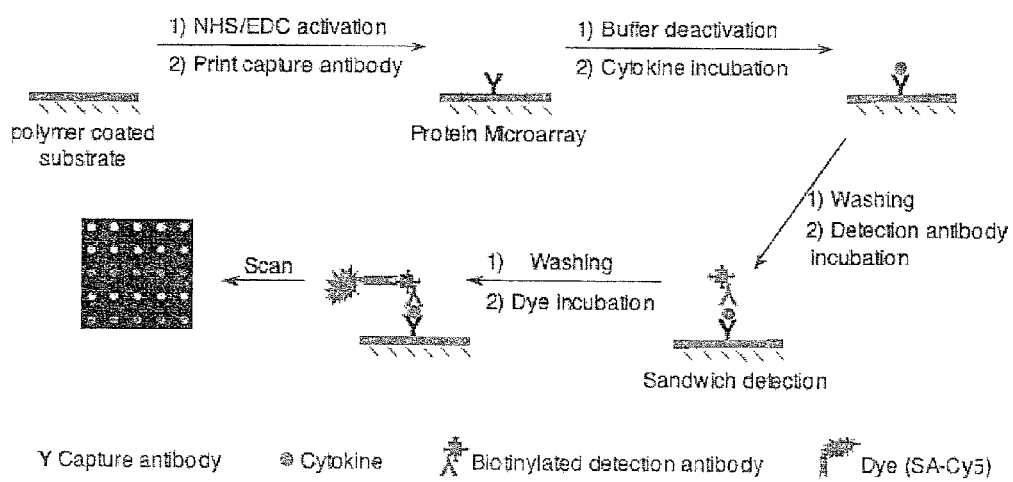
FIG. 2. Schematic representation of microarray fabrication By NHS?EDC coupling of antibodies to COOH-fucntionalized poly(OEGMA) brushes.
Figure 8:
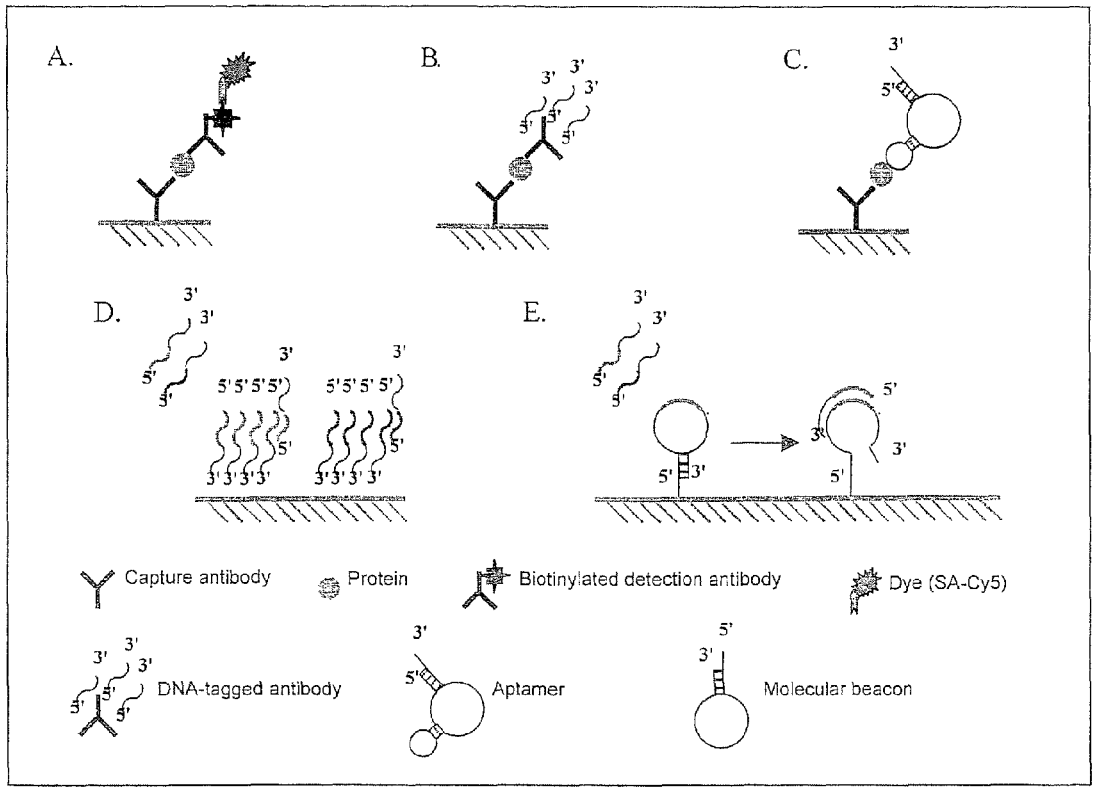
FIG. 8. Applications of TdTase-mediated DNA-extension signal amplification method.

The science community has recently witnessed an explosive development of microarray technique as one of the high-throughput screening strategies. Although with great success, the development of microarray technique is also accompanied with obstacles. One particular bottleneck for the development of microarray technique is the surface chemistry of microarray substrate. Typical materials used as microarray substrates, for example, poly(vinylidene fluoride), nitrocellulose, nylon, poly(L-lysine), silane, and ethylene-glycol self-assembled monolayer suffer from problems such as high level of nonspecific adsorption and/or low loading density (Zhu, Jun et al. 2001). Here, we have successfully demonstrated the "modular design of initiator" strategy to be generally applicable in creating non-fouling surfaces using poly (MAA-co-OEGMA) (FIG. 1). To highlight the potential applications of this non-fouling surface, we incorporated functional groups into the coating materials as binding sites and conjugated them with antibodies for the detection of cytokines in a microarray format (FIG. 2). Other detection schemes using DNA/RNA aptamers and enzymatic amplification can be easily incorporated into this surface modification platform to further improve the detection sensitivity (FIG. 8). Other than proteins, this technology is also applicable to micro- and nano-array detection systems for other biomolecules such as cDNA, (Schena, Shalon et al. 1995) small molecules, (MacBeath, Koehler et al. 1999) peptides, (Houseman, Huh et al. 2002) oligosaccharides, (Fukui, Feizi et al. 2002) and carbohydrates, (Houseman and Mrksich 2002; Wang, Liu et al. 2002), which have been demonstrated to be powerful tools in drug discovery, medical diagnostics, proteomic and genomic profiling, and other biotechnological applications.

FIG. 1. Schematic illustration of "SI-ATRP of OEGMA" strategy for creating functionalized non-fouling surfaces and molecular structure of silane initiator (11-(2-Bromo-2-methyl)propionyloxy)undecyl trichlorosilane. $SiO_2$ wafers were cleaned with a mixture of $NH_4OH:H_2O_2:H_2O$ (1:1:5, v/v/v) (Ma, Hyun et al. 2004) and glass slides were cleaned with a 1% RBS solution and a 1:1 (v/v) mixture of methanol:HCl before used immediately for silanization. Under $N_2$ atmosphere, the initiator-silane was deposited on silicon oxide substrate by vapor deposition and on cleaned glass slides by incubating with silane in anhydrous tetrahydrofuran. SI-ATRP was carried out as reported previously (Perruchot, Khan et al. 2001; Ma, Hyun et al. 2004). Briefly, under nitrogen, polymerization was initiated by adding the reaction mixture containing CuBr, bipyridine, and OEGMA in deionized water and methanol to the flask and was continued for a specified time. The samples were pulled out of the solution to stop the polymerization, rinsed with methanol and dried under flowing $N_2$ gas.

FIG. 2. Schematic representation of microarray fabrication. The carboxyl functionalized polymer coated slides were immersed into HCl solution and then NHS/EDAC solution. Each test slide was robotically printed with 12 identical 8×5 arrays using a Microsys 5100 microarrayer in an atmospherically controlled chamber. For each array, rows 1 and 8 were biotinylated BSA (B-BSA), regarded as positive control. Row 2 was BSA as negative control. Rows 3-7 were capture antibodies for human IL-1β, TNF-α, VEGF, IL-6, and TGF-β1, respectively. Prior to printing, the pin was sequentially cleaned in 5% Micro-Cleaning Solution. The printed arrays were immersed into sodium bicarbonate buffer (pH=8.5) for deactivation. Stock solutions of cocktail of cytokines/growth factors were prepared and diluted for dose-response studies. Each slide was directly incubated with cytokine solution. After three aspiration/wash cycles, each array was incubated with a cocktail containing a mixture of five biotinylated detection antibodies and then with streptavidin-Cy5. Finally, slides were scanned, imaged, and analyzed using a GenePix 4000B microarray scanner and GenePix 5.0 software.

Figure 3:
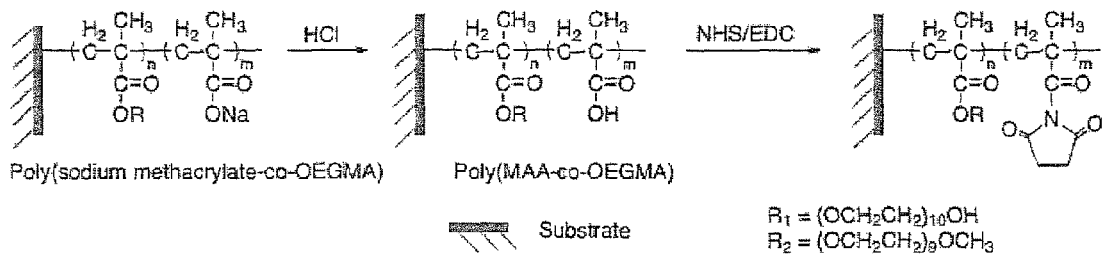
FIG. 3. Quasi-three dimensional, functionalized non-fouling films were prepared via SI-ATRP of OEGMA from modified glass slides.

FIG. 3. Quasi-three dimensional, functionalized non-fouling films were prepared via SI-ATRP of OEGMA from modified glass slides. Functionalized poly(OEGMA) films were prepared in one step by copolymerization of sodium methacrylate and methyl terminated OEGMA. In order to achieve a higher density, the silane initiator layer on glass was formed by dipping glass slides into silane initiator solution instead of vapor deposition. For copolymer poly(sodium methacrylate-co-OEGMA), the carboxylate was converted to carboxyl acid by incubation of copolymer in 1 M HCl, resulted in poly (MAA-co-OEGMA) (MAA: methyacrylate acid). This poly (MAA-co-OEGMA) was further converted to ester by incubation in N-hydroxysuccinimide/N-ethyl-N'-(3-dimethylaminopropyl) carbodiimide hydrochloride (NHS/EDC) solution.

Figure 4:
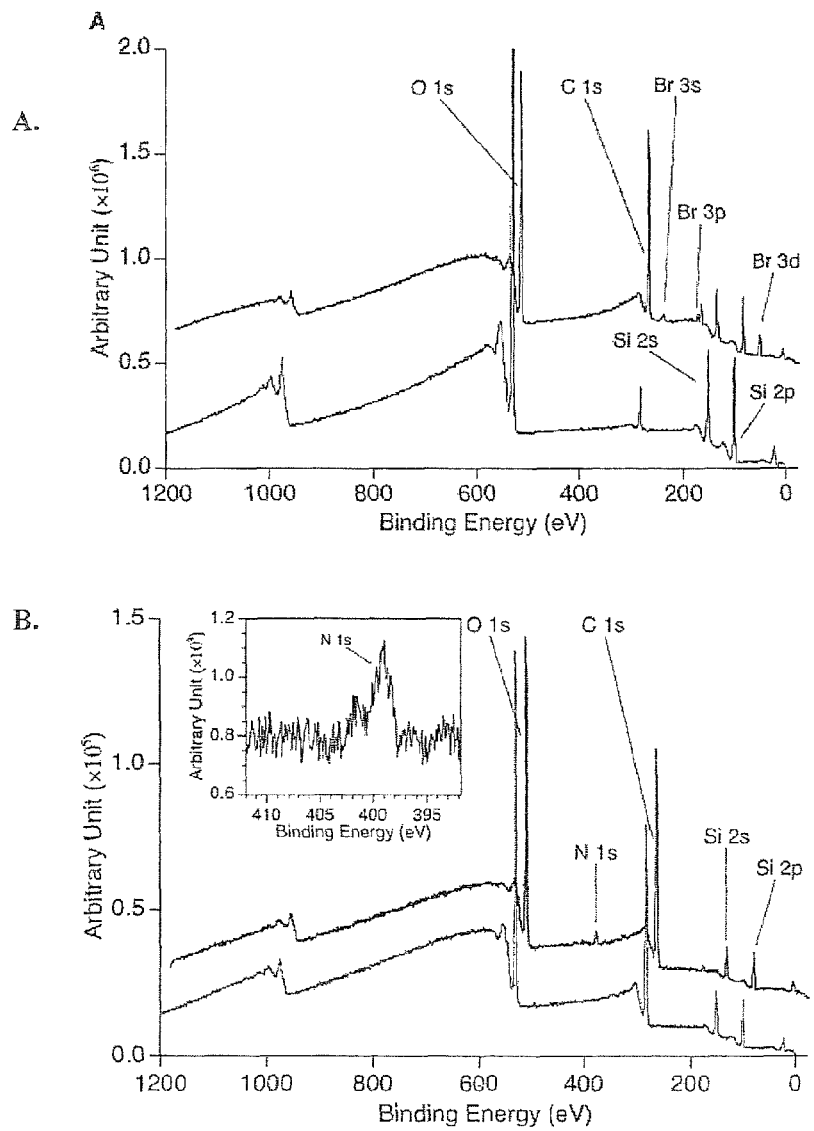
FIG. 4. The formation of initiator-silane SAM and poly(OEGMA) film confirmed by XPS.

FIG. 4. The formation of initiator-silane SAM and poly (OEGMA) film was confirmed by XPS (A). The polymerization introduced unique Br peaks (with an atomic percentage (AT. %) of ~5 AT. % based on $Br_{3d}$ at ~69 eV) at the low end of binding energy (BE) in the survey scan of initiator-silane SAM when compared with the spectrum of silicon oxide surface, and also increased carbon content from 1.2 to 49.3 AT. %. The later caused the AT. % of $Si_{2s}$ to drop from 18.3 for silicon oxide surface to 17.8 for a thin film and further down to 4.3 for a thick film due to enhanced attenuation effect posed by the increased poly(OEGMA) thickness. The poly (OEGMA) films (thickness of 95 Å) exhibited an XPS C/O ratio of 2.5, which is somewhat greater than the stoichiometric value of 2.1 for poly(OEGMA).

The polymerization and conversion of poly(sodium methacrylate-co-OEGMA) (thickness ~10 nm) was also confirmed by XPS study (B). Before and after NHS/EDC activation, survey scan showed no difference for poly(OEGMA) while the same treatment showed a new $N_{1s}$ peak at ~399 eV for functionalized copolymer coating. The final ratio of OEGMA and sodium methacrylate is determined using XPS core scan: one can roughly estimate the final composition to be 1/1.5 for OEGMA/sodium methacrylate, which is dramatically different from the initial feed ratio of 50/1. This radical change is probably due to the difference in polymerization kinetics for the two different species: OEGMA has a low incorporation rate because of its steric hindrance. The conversion of COOH to NHS is assumed to be 100%.

Figure 5:
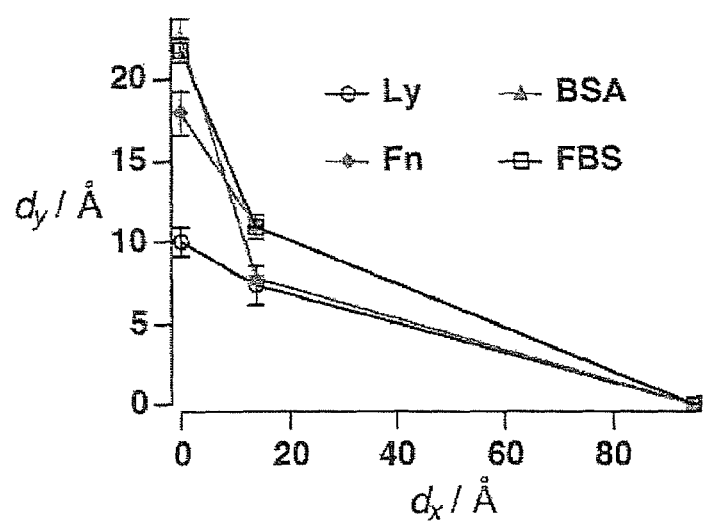
FIG. 5. The protein resistance of the poly(OEGMA) brushes was tested by the adsorption of fibronectin (Fn), bovine serum albumin (BSA), lysozyme (Ly) (all proteins at 1 mg/ml in PBS, pH=7.4), and undiluted fetal bovine serum (FBS).

FIG. 5. The protein resistance of the poly(OEGMA) brushes was tested by the adsorption of fibronectin (Fn), bovine serum albumin (BSA), lysozyme (Ly) (all proteins at 1 mg/ml in PBS, pH=7.4), and undiluted fetal bovine serum (FBS). Poly(OEGMA) modified and the control (initiator-modified) silicon wafers were immersed into a protein solution for 1 h, rinsed with buffer, dried under nitrogen stream, and the thickness of the adsorbed protein layer was measured by ellipsometry. The thickness of the protein layer ($d_y$) is a function of the poly(OEGMA) film thickness ($d_x$). The thickness of the adsorbed protein on the control surface varied depending upon the protein, ranging from ~10 Å (Ly) to ~25 Å for the other proteins and serum. In contrast, the poly (OEGMA) brush with ~14 Å thickness showed significantly less protein adsorption of all proteins and of serum. Increasing the thickness of the poly(OEGMA) brush to ~95 Å (and beyond, data not shown) eliminated the adsorption of all proteins and most notably that of serum to below the 1 Å detection limit of ellipsometry. These results are consistent with our previous results (Ma, Hyun et al. 2004) that a dense and thick poly(OEGMA) brush completely resists protein adsorption from solution.

Figure 6:
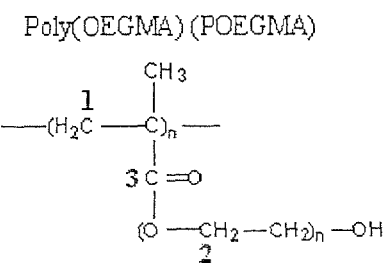
FIG. 6 Surface initiated polymerization of OEGMA can be directly carried out on a polymer substrate. (A) Chemical structures of Poly(OEGMA) and PVBC. Representative carbons are numbered to correspond with peaks in B. (B) XPS C(1s) spectra of PVBC coated substrates before (PVBC) and after (PVBC-POEGMA) SI-ATRP of OEGMA. The C(1s) spectrum of Poly(OEGMA) grown on silicon using a silane initiator (POEGMA) is shown for comparison. (C) Atomic percentages of carbon, oxygen and chlorine found in each sample.
Figure 6:
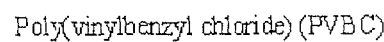
Figure 6:
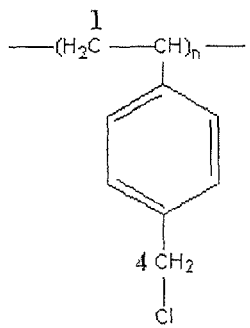
Figure 6:
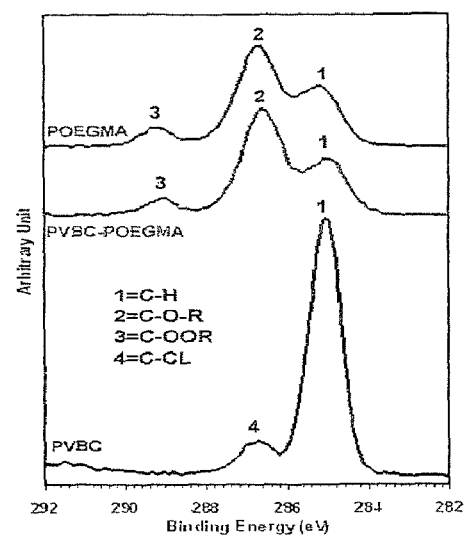

FIG. 6. OEGMA brushes were polymerized directly on a spun-cast film of poly(vinylbenzyl chloride) (PVBC) film without initiator to demonstrate that SI-ATRP can be performed on polymers in a straightforward and facile manner. Briefly, clean glass slides were treated with adhesion promoter hexamethyldisilazane followed by spinning on a 1% (w/v) solution of PVBC in toluene at 3000 rpm for one minute, and then drying at 80° C. for 20 min Ellipsometric measurements showed uniform PVBC film thicknesses of 35=1 nm. The OEGMA polymerization was carried out in an oxygen-free environment using CuBr/bipyridine as catalyst in a water/methanol mixture containing OEGMA monomer. Figure C.2.8B shows the XPS C(1s) spectra of PVBC coated substrates before (PVBC) and after (PVBC-POEGMA) SI-ATRP of OEGMA. The C(1s) spectrum of Poly(OEGMA) brushes grown on silicon using a silane initiator (POEGMA) is shown for comparison. The PVBC-POEGMA spectrum exhibits the formation of an ester peak at 289 eV, as well as a shift in the peaks at 286.7 and 285 eV, to closely mirror the spectrum of Poly(OEGMA) grown from silane initiator. Furthermore, the close match in carbon and oxygen atomic percentages found in the PVBC-POEGMA (70.5% C/29.0% O) and POEGMA (70.0% C/29.9% O) samples contrasted sharply with the atomic percentages found in the PVBC sample (91.5% C/0.5% O). The results indicate that halogenated polymers, be they intrinsic or covalently grafted, can be modified with a coating of poly(OEGMA) through the use of dip or spin coated halogenated films.

Figure 7:
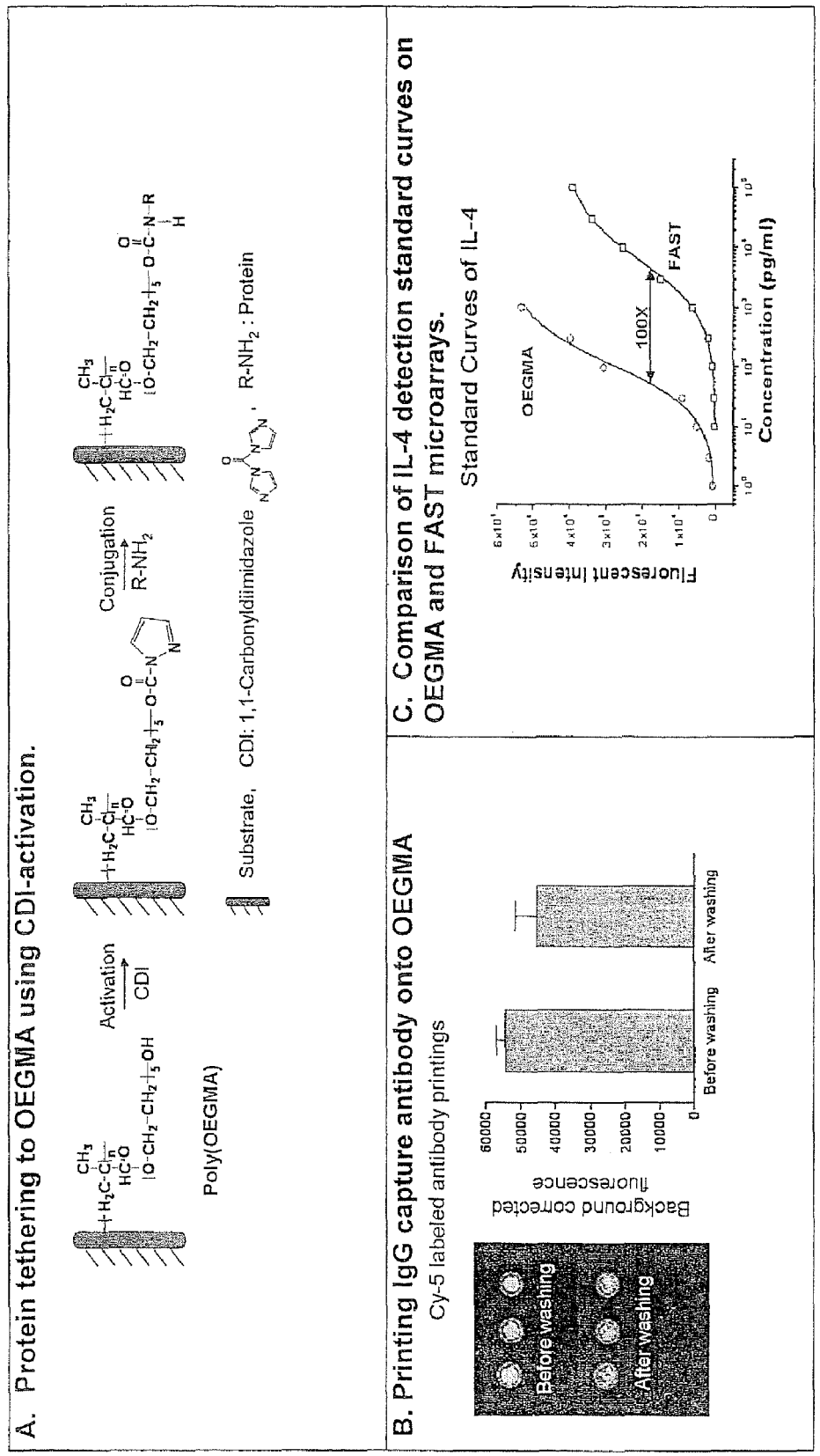
FIG. 7. Alternative embodiment of a protein microarray by printing of antibodies or other receptors to the polymer brush and their covalent attachment to activated OH groups of poly(OEGMA) brush. (A) Reaction scheme of coupling protein to CDI-activated OEGMA on glass. (B) Printing of an IgG capture antibody on brush and effect of washing of surface on spot stability. (C) Comparison of IL4 detection on poly(OEGMA) brush and on a FAST™ slide (Whatman).

FIG. 7. SI-ATRP of hydroxyl terminated OEGMA on glass and silicon yielded OEGMA films with an ellipsometric thickness of 10 nm. The hydroxyl groups of the polymer brush were then activated with a 0.5M solution of 1,1-Carbonyldiimidazole (CDI) in dry dioxane at 37° C. for 2 hours. The conversion of hydroxyl terminated OEGMA to OEGMA-CDI was confirmed by the appearance of a new N1s XPS peak at ~399 eV due to the presence of the imidazolyl carbamate group introduced during CDI activation. This intermediate imidazolyl carbamate is readily displaced by amine-containing proteins, resulting in stable carbamate linkages between OEGMA coatings and proteins. Attachment of proteins to the nonfouling OEGMA coatings on glass was achieved by introducing chemically reactive carbonyldiimidazole (CDI) groups into the polymerized brush. SI-ATRP of OEGMA yielded films of hydroxy-terminated ethylene glycol "stalks" on a methacrylate "core" (see FIG. 7A). Proteins were then conjugated through accessible amino groups FIG. 7B shows the fluorescence image of Cy-5 labeled anti-IL-4 capture antibody robotically printed and chemically tethered to CDI-activated OEGMA brushes on glass before and after a wash step. FIG. 7C compares the dose-response curves of IL-4 fluoroimmunoassay on CDT-activated OEGMA microarray and on a commercially available nitrocellulose microarray slide (FAST, Whatman). Features to note here are (1) the regions adjacent to the printed capture antibody in FIG. 6B are virtually black owing to the ultra-low background fluorescence of poly(OEGMA), (2) the poly(OEGMA) microarray is greater than 10-100× more sensitive than FAST slides owing to the complete resistance of the poly(OEGMA) to the non-specific adsorption of protein during the analyte incubation process, and (3) CDI immobilization chemistry clearly retains the activity of the tethered capture antibody (poly(OEGMA) microarrays can detect down to 1 pg/ml IL-4!).

FIG. 8. Applications of TdTase-mediated DNA-extension signal amplification method. The antibody-based sandwich-type protein detection scheme (A) can be easily combined or replaced with our technique. For example, the secondary antibody can be attached with short oligonucleotides (B) or substituted with an aptamer designed for a target molecule (C), and then extended at the 3' end by TdTase. For nucleic acid detection, target genes can be chemically grafted at their 3' end to a surface and cDNA that is hybridized to the target gene can be extended at its 3' end for signal amplification (D). In addition, molecular beacons containing target genes can be chemically grafted to a surface at their 5' end. The binding of cDNA to the target gene causes unfolding of the molecular beacon so that its 3' end becomes accessible for extension by TdTase (E).

Figure 9:
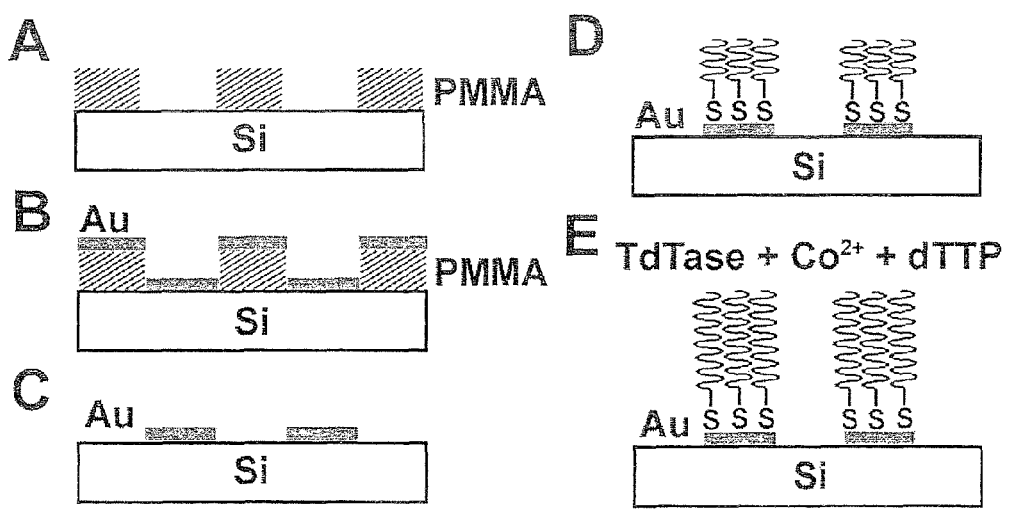
FIG. 9. Surface initiated extension of DNA by terminal transferase on biomolecular nanoarrays generated by e-beam lithography.

FIG. 9. Surface initiated extension of DNA by terminal transferase on biomolecular nanoarrays generated by e-beam lithography. An electron-sensitive resist layer (130 nm) of poly(methylmethacrylate) was spin-coated onto the cleaned Si substrate and annealed, and then patterned by exposure to an electron beam using a scanning electron microscope (A). A layer of chromium (50 Å) and a layer of gold (300 Å) were deposited by e-beam evaporation onto the patterned PMMA/Si to obtain geometrically well-defined gold features on the exposed $SiO_2$ surface (B). The gold-coated resist was lifted-off, leaving behind gold patterns of 35 nm height on the Si substrate (C). A self-assembled monolayer (SAM) of an oligonucleotide was prepared on the patterned gold arrays by incubation in a reduced DNA-thiol solution overnight (D). Enzymatic DNA extension was performed by incubating the patterned oligonucleotide arrays with TdTase in the presence of cobalt-containing buffer and 2'-deoxyguanosine 5'-triphosphate (dTTP) at 37° C. for 2 h (E).

Figure 10:
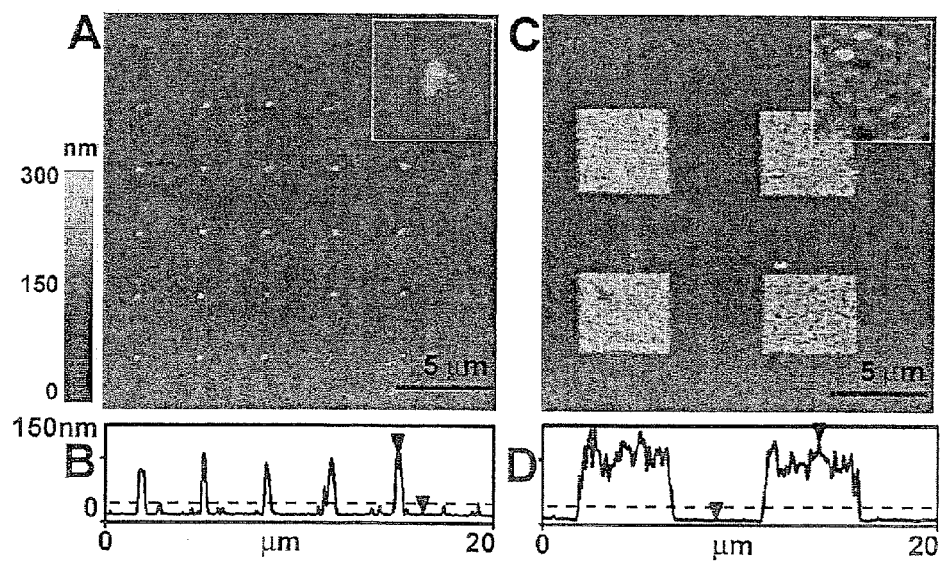
FIG. 10. Tapping mode AFM images in air for biomolecular arrays of different feature sizes (A-B: 0.1 µm; C-D: 4 µm) with 5'-SH—$(CH_2)_6$-T25 SAM after a 2-hour incubation with active terminal transferase (TdTase).

FIG. 10. Tapping mode AFM images in air for biomolecular arrays of different feature sizes (A-B: 0.1 μm; C-D: 4 μm) with 5'-SH—(CH2)6-T25 SAM after a 2-hour incubation with active terminal transferase (TdTase). Insets are the images of A and C at a higher magnification (1 μm×1 μm). B and D are the line profiles of A and C. Dotted lines represent the average height of gold arrays and immobilized DNA SAM. Poly(T) oligonucleotides were successfully extended on gold arrays with different lateral feature sizes. There are four significant observations from these experiments: (1) The average heights of the synthesized DNA nanostructures on gold features of 0.1 and 4 μm sides (minus the average height of gold arrays and immobilized DNA SAM) were 45.5±5.2 nm and 120.7±9.3 nm, respectively (B and D). The significant height increase suggests that the TdTase catalyzed polymerization of dTTP was successful. (2) The height of the DNA nanostructures grown by TdTase appears to be dependent upon the lateral feature size of the underlying gold patterns, with significantly lower extension observed for smaller feature size. This trend might be related to decreased steric accessibility of TdTase for the immobilized DNA as the feature size becomes smaller. (3) Images at a higher magnification for the 100 nm gold features showed that the DNA nanostructures had a lateral feature size of 358.5±10.0 nm (full width at half maximum, Figure A inset) and exhibited significant lateral extension. (4) DNA growth appeared to be heterogeneous and resulted in a layer of DNA with a RMS roughness of 13.6±0.6 nm for the 4 μm gold features (Figure C inset) vs. 0.23±0.02 nm for bare gold. In addition, these DNA nanostructures were less compact than those for 100 nm gold features, suggesting that their molecular weights were also affected by the lateral feature size.

Figure 11:
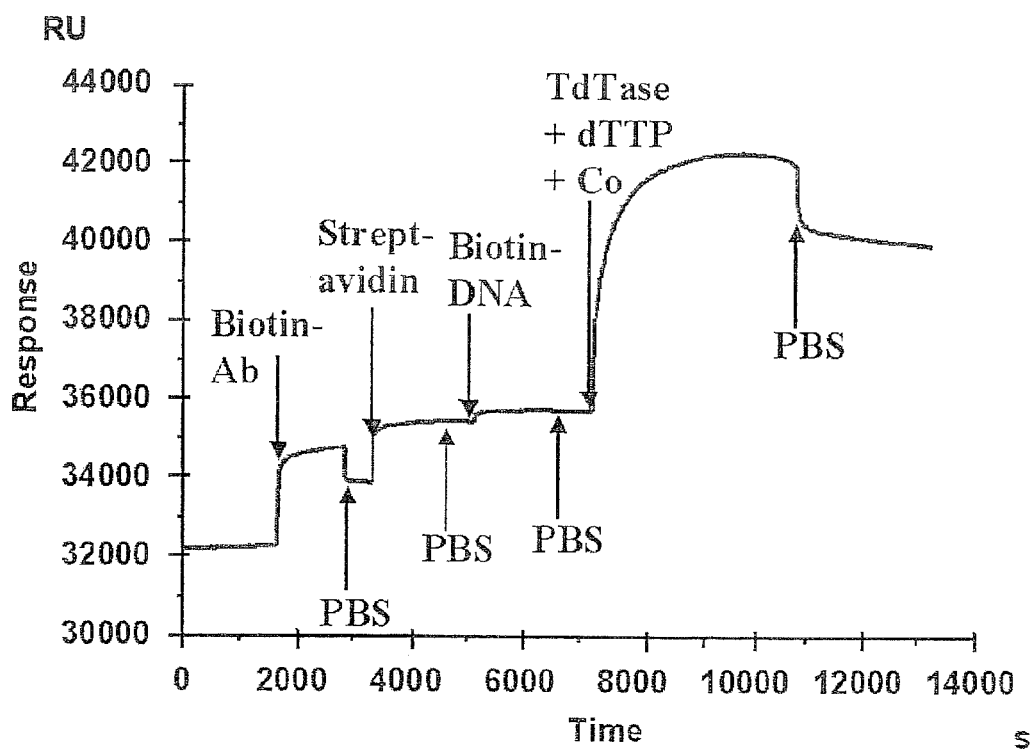
FIG. 11. SPR sensorgram for TdTase-mediated signal amplification with an antibody covalently conjugated with oligonucleotides.

FIG. 11. To test whether TdTase can extend oligonucleotides conjugated to an antibody, we ran a SPR experiment with a DNA-antibody complex conjugated through streptavidin-biotin interactions. Twenty microliters of biotinylated goat α-mouse antibody at 100 μg/ml was injected to a bare gold SPR chip (5 nm Cr and 35 nm Au), followed by a 10-minute PBS wash. Binding measurements and extension reactions were run at 37° C. at flowrate of 1 μl/min with PBS as washing buffer. Twenty microliters of streptavidin at 100 μg/ml, twenty microliters of biotin-$T_{25}$ at 10 μM, and sixty microliters of TdTase (0.6 U/μl) and dTTP (1 mM) in cobalt-containing buffer were injected sequentially, with a 10-minute PBS wash after each injection. There was an increase in RU of ~4,000, indicating that DNA conjugated on the antibody can be extended by TdTase (FIG. 3A).

In some embodiments, the present invention provides one or more of the following features:

1) Fast and stable immobilization. For most surface substrates, capture reagents are usually physisorbed on the surface. In contrast, poly(MAA-co-OEGMA) films provide a convenient way of covalently immobilizing capture reagents on the surface without protection and de-protection chemistry. The ester group (C(O)—NHS) is well known for fast protein coupling (Hermanson 1996) and can be easily introduced to the poly(MAA-co-OEGMA) platform through a two-step chemistry (FIG. 2). The superior tolerance of surface-initiated atom transfer radical polymerization (SI-ATRP) to functional groups exhibited in this case as the direct introduction of COOH terminal functional group. The reaction has been demonstrated to complete within a few seconds under a moisturized environment instead of aqueous surrounding (Hyun, Ahn et al. 2002). The excess C(O)—NHS groups can be easily deactivated by incubation of sodium bicarbonate buffer (pH=8.5), which is better than aldehyde slides that used BSA to neutralize (MacBeath and Schreiber 2000). To further optimize the polymer matrix, methyl terminated OEGMA (n=9) and OH terminated OEGMA (n=12) were copolymerized. The different n values were chosen so that OH functional will be more accessible for the immobilization of protein and other ligands. The OH functional group can either be directly used or be further converted to COOH group as demonstrated in our previous paper (Hyun, Ma et al. 2002). In an alternative approach, proteins can be coupled through their amine groups to the OH groups present in the poly(OEGMA) after activation of the OH groups using CDI (Hermanson 1996) (FIG. 7A). This approach gives consistent and reproducible attachment of proteins.

2) Low and consistent background. Poly(MAA-co-OEGMA), unlike nitrocellulose-coated, aldehyde-coated, epoxy-coated and silylated slides (Li, Nath et al. 2003; Li and Reichert 2003), has minimal level of auto-fluorescence emission, of which majority is originated from the underlying glass substrate. In addition, poly(MAA-co-OEGMA) films showed no sign of nonspecific adsorption of detection reagents (antibodies) to substrates (FIGS. 5 and 6). The same is true of the CDI-activated protein microarray, as seen in FIG. 7C. These films also showed a consistent level of background, regardless of cytokine concentration (10 pg/ml to 10 ng/ml), even for cytokines in serum (~55 mg/ml protein mixture) (Elbert and Hubbell 1996), or *E. coli* lysate, and is very close to their unprocessed counterpart, even without any blocking step. The overall background of poly(MAA-co-OEGMA)-coated surfaces and other similar functionalized poly(OEGMA)-based matrixes is 100 times lower than that of nitrocellulose-coated one (FAST™ slides). The advantages of low and consistent background are: 1) it enables the detection of a target biomolecule in complex biological fluids such as whole blood, serum, or cell lysate and 2) low auto fluorescence also improves detection sensitivity and increases the detection limit for various assays. Current detection limits of better than 0.1 pg/ml cytokine can be easily achieved.

3) High loading density. The loading density of capture reagent, target biomolecules, and detection reagent is substantially increased as a result of the increased surface to volume ratio for the quasi three dimensional poly(MAA-co-OEGMA) films (FIG. 2) when compared with planar EG-SAM based substrates (Houseman and Mrksich 2002), but lower than the 3D gel pad system, which unfortunately suffers from the problem of high level of nonspecific adsorption (Arenkov, Kukhtin et al. 2000). OEG terminated SAM (Houseman and Mrksich 2002) as well as PLL-g-PEG (Ruiz-Taylor, Martin et al. 2001) system have been used but showed limited success. The former suffered from low loading density and the later suffered from poor performance under complex solution (FBS) due to its low density of PEG coating as well as limited stability.

4) Applicable for biomolecular detection in the microarray and nanoarray format. The ultra-low background of poly (MAA-co-OEGMA) films not only eliminates the need of blocking, but also significantly improves the quality of the signal originated from the target biomolecules (FIGS. 2 and 7). Bovine serum albumin (BSA) is widely used as a blocking material but there is evidence shown that adsorbed BSA affects protein binding or ligand-receptor interaction (MacBeath, Koehler et al. 1999). The elimination of the blocking step provides substantial benefit for biomolecular detection, especially for microarrays with spot size of sub-micron length scale, where the signal-to-noise ratios can be severely reduced by the presence of BSA molecules.

5) Application to other receptor-analyte pairs. The sandwich-type detection scheme employed on our poly(MAA-co-OEGMA) platform is not limited to the use of antibodies as capture and detection agents. Other detection modalities such as DNA/RNA aptamers can be easily incorporated and further modified to the detection of other biomolecules. The advantages of using DNA/RNA aptamers are their superior thermal and chemical stability, lower cost of synthesis, and ease of modification to achieve high binding affinity (Bock, Griffin et al. 1992; Macaya, Schultze et al. 1993).

6) Signal amplification for antibody-based biomolecular detection. To achieve ultra-high sensitivity, we developed an amplification technique with terminal deoxynucleotidyl transferase (TdTase), an enzyme that repeatedly adds mononucleotides to the 3' end of single- or double-stranded DNA/RNA (FIG. 8). The addition of these nucleotides at their 3' end of the target DNA significantly increases the detectable signal. There are several ways that we can combine or replace antibody-based sandwich-type protein detection methods with signal amplification by TdTase-mediated DNA extension: 1) secondary antibodies can be attached with short oligonucleotides, which are amplified by TdTase. Short oligonucleotides can be randomly attached to lysine resides of antibodies or site-specifically attached to the Fc region only, so that the extension of multiple oligonucleotides on the antibody would provide further signal amplification, and 2) secondary antibodies can be completely replaced with an aptamer designed for a target molecule, which is then extended at its 3' end by TdTase.

7) Signal amplification for DNA-based biomolecular detection. For the ultra-sensitive nucleic acid detection such as DNA microarray, target genes can be chemically grafted at their 3' end to a poly(MAA-co-OEGMA)-coated surface and cDNA prepared from a sample that is hybridized to the target gene can be extended at its 3' end for signal amplification (FIG. 8). In addition, molecular beacons without fluorophores containing target genes can be chemically grafted at their 5' end (FIG. 8). The binding of cDNA in a sample to the target gene causes unfolding of the molecular beacon so that its 3' end is no longer hybridized to another part of the beacon and becomes accessible for extension by TdTase. This triggered approach can potentially further cut down background.

8) Highly adaptable to a variety of detection methods. Signals amplified by TdTase can be detected by a variety of methods: 1) direct detection of the unlabeled DNA tag using the atomic force microscopy (AFM) (FIGS. 9 and 10), direct detetcio using SPR spectroscopy (FIG. 11) 3) incorporate radiolabeled nucleotides (3H, 14C, and 32P) directly in growing DNA chain for radioactive detection, 4) incorporate stable isotope labeled nucleotides in growing DNA chain and detect by time-of-flight secondary-ion mass spectrometry (ToF-SIMS) or matrix-assisted laser desorption/ionization mass spectrometry (MALDI-MS), 5) incorporate fluorophores directly into the DNA chain followed by fluorescence detection, 6) incorporate nucleotides containing amino acids, to which fluorophores are attached, for more efficient attachment than with fluorophore-labeled nucleotides, and 7) indirect detection by hybridization of the extended DNA tag with a complementary full-length DNA strand or short oligonucleotides functionalized with metal nanoparticles, quantum dots, fluorophores, or radionuclides without directly incorporating labeled nucleotides into the DNA chain.

REFERENCES

(1) U.S. Patent Documents

1. U.S. Pat. No. 6,867,289 Gorenstein, David G.; Luxon, Bruce A.; Herzog, Norbert; Aronson, Judy, Thio-modified aptamer synthetic methods and compositions.
2. U.S. Pat. No. 6,815,078 Qiao, Tiecheng A.; Leon, Jeffrey W.; Penner, Thomas L.; Yang, Zhihao, Substrate for protein microarray containing functionalized polymer.
3. U.S. Pat. No. 6,582,926 Chilkoti, Ashutosh, Methods of using bioelastomers.
4. U.S. Pat. No. 6,444,254 Chilkoti, Ashutosh; Yang, Zhongping, Microstamping activated polymer surfaces.
5. U.S. Pat. No. 5,840,867 Toole, John J.; Griffin, Linda C.; Bock, Louis C.; Latham, John A., Aptamer analogs specific for biomolecules.
6. U.S. Pat. No. 5,582,981 Toole, John J.; Latham, John; Bock, Louis C.; Griffin, Linda C., Method for identifying an oligonucleotide aptamer specific for a target.

(2) Other References

Arenkov, P., A. Kukhtin, et al. (2000). "Protein microchips: Use for immunoassay and enzymatic reactions." *Analytical Biochemistry* 278(2): 123-131.
Bock, L. C., L. C. Griffin, et al. (1992). "Selection Of Single-Stranded-Dna Molecules That Bind And Inhibit Human Thrombin." *Nature* 355(6360): 564-566.
Elbert, D. L. and J. A. Hubbell (1996). "Surface Treatments of Polymers for Biocompatibility." *Annu Rev. Mater. Sci.* 26: 365-394.
Emoto, K., J. M. Hauls, et al. (1996). "Grafting poly(ethylene glycol) epoxide to amino-derivatized quartz: Effect of temperature and pH on grafting density."*Analytical Chemistry* 68(21): 3751-3757.
Fukui, S., T. Feizi, et al. (2002). "Oligosaccharide microarrays for high-throughput detection and specificity assignments of carbohydrate-protein interactions." *Nature Biotechnology* 20(10): 1011-1017.
Hermanson, G. T. (1996). *Bioconjugate Techniques*. San Diego, Academic Press.
Houseman, B. T., J. H. Huh, et al. (2002). "Peptide chips for the quantitative evaluation of protein kinase activity." *Nature Biotechnology* 20(3): 270-274.
Houseman, B. T. and M. Mrksich (2002). "Carbohydrate arrays for the evaluation of protein binding and enzymatic modification." *Chemistry & Biology* 9(4): 443-454.
Hyun, J., S. Ahn, et al. (2002). "Molecular recognition-mediated fabrication of protein nanostructures by dip-pen lithography." *Nanoletters* 2(11): 1203-1207.
Hyun, J., H. Ma, et al. (2002). "Micropatterns of a cell-adhesive peptide on an amphiphilic comb polymer film." *Langmuir* 18(8): 2975-2979.
Kingshott, P., H. Thissen, et al. (2002). "Effects of cloud-point grafting, chain length, and density of PEG layers on competitive adsorption of ocular proteins." *Biomaterials* 23(9): 2043-2056.
Knoll, D. and J. Hermans (1983). "Polymer-protein interactions—comparison of experiment and excluded volume theory." *Journal of Biological Chemistry* 258(9): 5710-5715.
Li, Y. W., N. Nath, et al. (2003). "Parallel comparison of sandwich and direct label assay protocols on cytokine detection protein arrays." *Analytical Chemistry* 75(19): 5274-5281.
Li, Y. W. and W. M. Reichert (2003). "Adapting cDNA microarray format to cytokine detection protein arrays." *Langmuir* 19(5): 1557-1566.
Ma, H., J. Hyun, et al. (2004). ""Non-fouling" oligo(ethylene glycol)-functionalized polymer brushers synthesized by surface-initiated atom transfer radical polymerization." *Advanced Materials* 16(No. 4): 338-341.
Macaya, R. F., P. Schultze, et al. (1993). "Thrombin-Binding Dna Aptamer Forms A Unimolecular Quadruplex Structure In Solution." *Proceedings Of The National Academy Of Sciences Of The United States Of America* 90(8): 3745-3749.
MacBeath, G., A. N. Koehler, et al. (1999). "Printing small molecules as microarrays and detecting protein-ligand interactions en masse." *Journal of the American Chemical Society* 121(34): 7967-7968.
MacBeath, G. and S. L. Schreiber (2000). "Printing proteins as microarrays for high-throughput function determination." *Science* 289(5485): 1760-1763.
Nagasaki, Y., T. Ishii, et al. (2001). "PEG-modified Nanoparticles for New Molecular Recognition." *European Cells and Materials* 6. Suppl. 1: 23.
Perruchot, C., M. A. Khan, et al. (2001). "Synthesis of well-defined, polymer-grafted silica particles by aqueous ATRP." *Langmuir* 17(15): 4479-4481.
Ratner, B., F. Schoen, et al. (1996). *Biomaterials science: an introduction to materials in medicine*. San Diego, Academic Press.
Ruiz-Taylor, L. A., T. L. Martin, et al. (2001). "Monolayers of derivatized poly(L-lysine)-grafted poly(ethylene glycol)

on metal oxides as a class of biomolecular interfaces." *Proceedings of the National Academy of Sciences of the United States of America* 98(3): 852-857.

Schena, M., D. Shalon, et al. (1995). "Quantitative Monitoring of Gene-Expression Patterns with a Complementary-DNA Microarray." *Science* 270(5235): 467-470.

Seeberger, P. H. and W. C. Haase (2000). "Solid-phase oligosaccharide synthesis and combinatorial carbohydrate libraries." *Chemical Reviews* 100(12): 4349-4393.

StJohn, P. M. and H. G. Craighead (1996). "Microcontact printing and pattern transfer using trichlorosilanes on oxide substrates." *Applied Physics Letters* 68(7): 1022-1024.

Ulman, A. (1996). "Formation and structure of self-assembled monolayers." *Chemical Reviews* 96(4): 1533-1554.

Vijayendran, R. A. and D. E. Leckband (2001). "A quantitative assessment of heterogeneity for surface-immobilized proteins." *Analytical Chemistry* 73(3): 471-480.

Wang, D. N., S. Y. Liu, et al. (2002). "Carbohydrate microarrays for the recognition of cross-reactive molecular markers of microbes and host cells." *Nature Biotechnology* 20(3): 275-281.

Wasserman, S. R., Y. T. Tao, et al. (1989). "Structure and reactivity of alkylsiloxane monolayers formed by reaction of alkyltrichlorosilanes on silicon substrates." *Langmuir* 5(4): 1074-1087.

Xia, Y. N., M. Mrksich, et al. (1995). "Microcontact Printing of Octadecylsiloxane on the Surface of Silicon Dioxide and Its Application in Microfabrication." *Journal of the American Chemical Society* 117(37): 9576-9577.

Yang, Z. H., J. A. Galloway, et al. (1999). "Protein interactions with poly(ethylene glycol) self-assembled monolayers on glass substrates: Diffusion and adsorption." *Langmuir* 15(24): 8405-8411.

Zhu, H. and M. Snyder (2003). "Protein chip technology." *Current Opinion in Chemical Biology* 7(1): 55-63.

Zhu, X., Y. Jun, et al. (2001). "Grafting of high-density poly (ethylene glycol) monolayers on Si(111)." *Langmuir* 17(25): 7798-7803.

Zhu, X. Y., Y. Jun, et al. (2001). "Grafting of high-density poly(ethylene glycol) monolayers on Si(111)." *Langmuir* 17(25): 7798-7803.

The foregoing is illustrative of the present invention, and is not to be construed as limiting thereof. The invention is defined by the following claims, with equivalents of the claims to be included therein.

That which is claimed is:

1. A method of making a biomolecular detector, said method comprising:
   (a) providing a substrate having a surface portion;
   (b) depositing a linking layer on said surface portion; and
   (c) forming a polymer layer on said linking layer by the process of surface-initiated polymerization of monomeric units thereon, with each of said monomeric units comprising a monomer core group having at least one protein-resistant head group coupled thereto, to thereby form a brush molecule on said surface portion;
   said brush molecule comprising a stem formed from the polymerization of said monomer core groups, and a plurality of branches formed from said head group projecting from said stem; and then
   (d) covalently coupling a member of a specific binding pair to said polymer layer.

2. The method of claim 1, wherein said polymer comprises a copolymer of methoxy-terminated OEGMA and hydroxy-terminated OEGMA.

3. The method of claim 2, further comprising coupling a compound having an amine group to said hydroxy group via said amine group.

4. The method of claim 3, wherein said copolymer is synthesized on said surface portion by SI-ATRP, wherein said hydroxy groups are converted to COOH groups by reaction with N-hydroxy succinimide (NHS), and wherein said amine groups are coupled to said COOH.

5. The method of claim 1, wherein said polymer comprises a copolymer of OEGMA and sodium methacrylate, said copolymer having sodium carboxylate groups.

6. The method of claim 5, where said sodium carboxylate group is converted to a COOH group by reaction with HCl, and a protein or peptide is coupled to said COOH groups via their N-terminal amine or lysine residues with NHS/EDC coupling.

7. The method of claim 1, wherein said polymer is OEGMA, said OEGMA containing thioester groups; and wherein said member of a specific binding pair is coupled to said thioester group.

8. The method of claim 1, wherein said member of a specific binding pair is a protein or peptide having an N-terminal cysteine, and wherein said coupling step is carried out by reaction with said N-terminal cysteine with said thioester by intein protein ligation (IPL) or native chemical ligation.

9. The method of claim 1, wherein said polymer is OEGMA, said OEGMA contains cysteine groups, said member of a specific binding pair contains a C-terminal thioester, and said coupling step is carried out by reaction of said C-terminal cysteine with said thioester by intein protein ligation (IPL) or native chemical ligation.

10. The method of claim 1, wherein said surface portion comprises a material selected from the group consisting of metals, metal oxides, semiconductors, polymers, silicon, silicon oxide, and composites thereof.

11. The method of claim 1, wherein said surface portion comprises gold.

12. The method of claim 1, wherein said linking layer is continuous.

13. The method of claim 1, wherein said linking layer is patterned.

14. The method of claim 1, wherein said linking layer is a self-assembled monolayer.

15. The method of claim 1, wherein said brush molecule is from 5 to 50 nanometers in length.

16. The method of claim 1, wherein said brush molecule is formed on said surface portion at a density from 40 to 100 milligrams per meter$^2$.

17. The method of claim 1, wherein said brush molecule is produced by surface-initiated atom transfer radical polymerization of oligo(ethylene glycol)methyl methacrylate.

* * * * *